(12) United States Patent
Herrig

(10) Patent No.: US 11,033,678 B2
(45) Date of Patent: Jun. 15, 2021

(54) COMPACT INJECTOR DRIVE

(71) Applicant: ACIST MEDICAL SYSTEMS, INC., Eden Prairie, MN (US)

(72) Inventor: Judson A. Herrig, Elko New Market, MN (US)

(73) Assignee: AGIST MEDICAL SYSTEMS, INC., Eden Prairie, MN (US)

( * ) Notice: Subject to any disclaimer, the term of this patent is extended or adjusted under 35 U.S.C. 154(b) by 0 days.

(21) Appl. No.: 16/194,986

(22) Filed: Nov. 19, 2018

(65) Prior Publication Data

US 2019/0151532 A1 May 23, 2019

Related U.S. Application Data

(60) Provisional application No. 62/588,577, filed on Nov. 20, 2017.

(51) Int. Cl.
*A61M 5/145* (2006.01)
*A61M 5/00* (2006.01)
*A61M 5/315* (2006.01)

(52) U.S. Cl.
CPC .......... *A61M 5/1452* (2013.01); *A61M 5/007* (2013.01); *A61M 5/1454* (2013.01); *A61M 5/14546* (2013.01); *A61M 2005/14506* (2013.01); *A61M 2005/31518* (2013.01)

(58) Field of Classification Search
CPC ...... A61M 2005/31518; A61M 5/1454; A61M 2005/14506; A61M 5/1452; A61M 5/14546
See application file for complete search history.

(56) References Cited

U.S. PATENT DOCUMENTS

| 1,165,686 | A | 12/1915 | McElroy |
| 1,348,796 | A | 8/1920 | Gronbech |
| 3,147,753 | A | 9/1964 | Nogier et al. |

(Continued)

FOREIGN PATENT DOCUMENTS

| EP | 302248 A1 | 2/1989 |
| EP | 599649 A1 | 6/1994 |

(Continued)

OTHER PUBLICATIONS

ACIST CVi Contrast Delivery System User Manual, (P/N 900420-001 Rev. 4), Nov. 2005, 91 pages.

*Primary Examiner* — Atif H Chaudry
(74) *Attorney, Agent, or Firm* — Fredrikson & Byron, P.A.

(57) ABSTRACT

In one embodiment, an injector includes a sleeve, a drive assembly, and a drive assembly housing. The sleeve is configured to receive a reservoir having a plunger therein. The drive assembly is configured to pressurize the reservoir and includes a tip, an actuator, and mechanical segments. The tip is configured to be secured to the plunger. The actuator is configured to supply a motive force to the tip for moving it between retracted and extended positions. The mechanical segments are configured to transmit motive force from the actuator to the tip. The drive assembly housing has a housing length in a direction parallel to a central longitudinal axis of the tip. The reservoir has a reservoir length L. A package length is defined by the housing length and the reservoir length L. The package length is less than 2L.

15 Claims, 5 Drawing Sheets

(56) References Cited

U.S. PATENT DOCUMENTS

| | | |
|---|---|---|
| 3,742,949 A | 7/1973 | Hill |
| 3,890,956 A | 6/1975 | Moorehead |
| 4,215,701 A | 8/1980 | Raitto |
| 4,266,557 A | 5/1981 | Merry |
| 4,869,720 A | 9/1989 | Chernack |
| 4,952,208 A | 8/1990 | Lix |
| 5,007,904 A | 4/1991 | Densmore et al. |
| 5,085,638 A | 2/1992 | Farbstein et al. |
| 5,181,912 A | 1/1993 | Hammett |
| 5,299,559 A * | 4/1994 | Bruce .................. A61B 1/0052 600/141 |
| 5,314,416 A | 5/1994 | Lewis et al. |
| 5,383,858 A | 1/1995 | Reilly et al. |
| 5,411,489 A | 5/1995 | Pagay et al. |
| 5,453,093 A | 9/1995 | Haining |
| 5,620,423 A | 4/1997 | Eykmann et al. |
| 5,735,825 A | 4/1998 | Stevens et al. |
| 5,875,976 A | 3/1999 | Nelson et al. |
| 5,947,929 A | 9/1999 | Trull |
| 6,511,459 B1 | 1/2003 | Fago |
| 6,752,789 B2 | 6/2004 | Duchon et al. |
| 7,547,297 B2 | 6/2009 | Brinkhues |
| 7,797,932 B2 | 9/2010 | Herrick et al. |
| 8,118,781 B2 | 2/2012 | Knopper et al. |
| 8,540,683 B2 | 9/2013 | Williams, Jr. et al. |
| 8,613,730 B2 | 12/2013 | Hieb et al. |
| 9,352,105 B2 | 5/2016 | Hieb et al. |
| 9,925,338 B2 | 3/2018 | Hieb et al. |
| 2002/0022807 A1 | 2/2002 | Duchon et al. |
| 2004/0122369 A1 | 6/2004 | Schriver et al. |
| 2006/0069356 A1 | 3/2006 | Witowski |
| 2008/0183131 A1 | 7/2008 | Duchon et al. |
| 2013/0096495 A1 * | 4/2013 | Holmqvist .......... A61M 5/2066 604/89 |
| 2018/0304014 A1 * | 10/2018 | Knudsen ................ A61M 5/326 |
| 2019/0328973 A1 * | 10/2019 | Cowe .................. A61M 5/2429 |

FOREIGN PATENT DOCUMENTS

| | | |
|---|---|---|
| JP | H07313598 A | 12/1995 |
| JP | 2001507963 A | 6/2001 |
| JP | 2001520087 A | 10/2001 |
| JP | 2005511158 A | 4/2005 |
| WO | 9201485 A1 | 2/1992 |
| WO | 9630066 A1 | 10/1996 |
| WO | 9920330 A1 | 4/1999 |
| WO | 9955401 A1 | 11/1999 |
| WO | 02096487 A1 | 12/2002 |
| WO | 2007062315 A2 | 5/2007 |
| WO | 2008134751 A1 | 11/2008 |
| WO | 2010062804 A1 | 6/2010 |
| WO | 2010062807 A1 | 6/2010 |

* cited by examiner

COMPACT INJECTOR DRIVE

RELATED APPLICATION

This application claims the benefit of U.S. Provisional Application No. 62/588,577 filed Nov. 20, 2017, the contents of which are hereby incorporated by reference.

TECHNICAL FIELD

This disclosure generally relates to powered fluid injectors as well as related methods of pressurizing a fluid in a powered fluid injector.

BACKGROUND

Many medical procedures, including diagnostic and/or interventional procedures, involve injecting a contrast media into a patient. Angiography is one example of such a procedure. Angiography is used in the diagnosis and treatment of cardiovascular conditions including abnormalities or restrictions in blood vessels. During angiography, a radiographic image of the heart or vascular structure is obtained by injecting contrast media through a catheter into a vein or artery of the patient. The injected contrast media can pass to vascular structures in fluid communication with the vein or artery in which the injection is made. Electromagnetic energy (e.g., X-rays, radio waves (e.g., magnetic resonance imaging), or ultrasonic waves) is passed through the region of the body in which the contrast media was injected. This energy is absorbed by the contrast media, causing a radiographic outline or image of the blood vessel containing the contrast media.

An injector can be used to inject contrast media into a patient in conjunction with diagnostic and/or interventional medical procedures. Contrast media is generally held at the injector within a fluid container, such as a reservoir. During a patient injection, the injector pressurizes and delivers this contrast media to the patient. To do so, the injector generally drives a shaft linearly within the fluid container, starting at one end of the fluid container and moving progressively through the fluid container to an opposite end. So that the injector can deliver all of the contrast media in the fluid container, the shaft generally has a fixed length extending in linear alignment with the fluid container at least equal to a length of the fluid container. Moreover, components used for linearly driving the shaft add to this length. Accordingly, a spatial profile created by the length of the fluid container, shaft, and drive components can be more than twice the length of the fluid container itself. Because space in the vicinity of a patient undergoing a medical procedure can be at a premium, this size of a typical injector may be undesirable.

SUMMARY

In general, various exemplary embodiments relating to powered fluid injectors, and related methods of pressurizing a fluid, are disclosed herein. These embodiments can be useful, for instance, by providing a compact powered fluid injector. This can be valuable since a compact powered fluid injector can create additional available space in the vicinity of a patient undergoing a medical procedure. This additional available space can accommodate medical personnel and/or other medical devices as needed for a particular medical procedure. Yet, the powered fluid injector and related method embodiments disclosed herein can still be capable of providing operational functionality associated with traditional, less compact injectors.

One exemplary embodiment includes a powered fluid injector. This exemplary powered fluid injector embodiment includes a sleeve, a drive assembly, and drive assembly housing. The sleeve is configured to receive a reservoir that includes an inner reservoir diameter and a reservoir length L defining an internal reservoir volume and a plunger within the internal reservoir volume. The drive assembly is configured to pressurize the internal reservoir volume. The drive assembly includes a tip, an actuator, and a plurality of mechanical segments. The tip has a central longitudinal axis and is configured to be secured to the plunger. The tip has a retracted position and an extended position. The actuator is configured to supply a motive force to the tip for moving the tip between the retracted and extended positions. The plurality of mechanical segments are configured to transmit the motive force from the actuator to the tip. The drive assembly housing has a housing length in a direction parallel to the central longitudinal axis, a housing width in a first direction perpendicular to the central longitudinal axis, and a housing height in a second direction perpendicular to the central longitudinal axis. The actuator is positioned within the drive assembly housing. The plurality of mechanical segments are positioned within the drive assembly housing when the tip is in the retracted position. The housing length and the reservoir length L define a package length extending in the direction parallel to the central longitudinal axis. The package length is less than 2L.

In a further exemplary embodiment of this powered fluid injector, the plurality of mechanical segments includes a first segment portion and a second segment portion. The first segment portion is along the central longitudinal axis of the tip and the second segment portion is offset from the central longitudinal axis of the tip. The first and second segment portions can be positioned as such, for instance, when the tip is in the retracted position.

Another exemplary embodiment includes a method of pressurizing fluid at a powered fluid injector. This exemplary method embodiment includes actuating a drive assembly of the powered fluid injector to supply a motive force for moving a tip of the drive assembly between a retracted position and an extended position. This tip is configured to be secured to a plunger that is within an internal volume of a reservoir. The exemplary method further includes moving the tip from the retracted position to the extended position by moving a portion of the drive assembly from a first location that is offset from a central longitudinal axis of the tip to a second location that is along the central longitudinal axis of the tip. The exemplary method also includes moving the tip from the extended position to the retracted position by moving the portion of the drive assembly from the second location to the first location.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following description. Embodiments of the invention will hereinafter be described in conjunction with the appended drawings.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Figure 1:
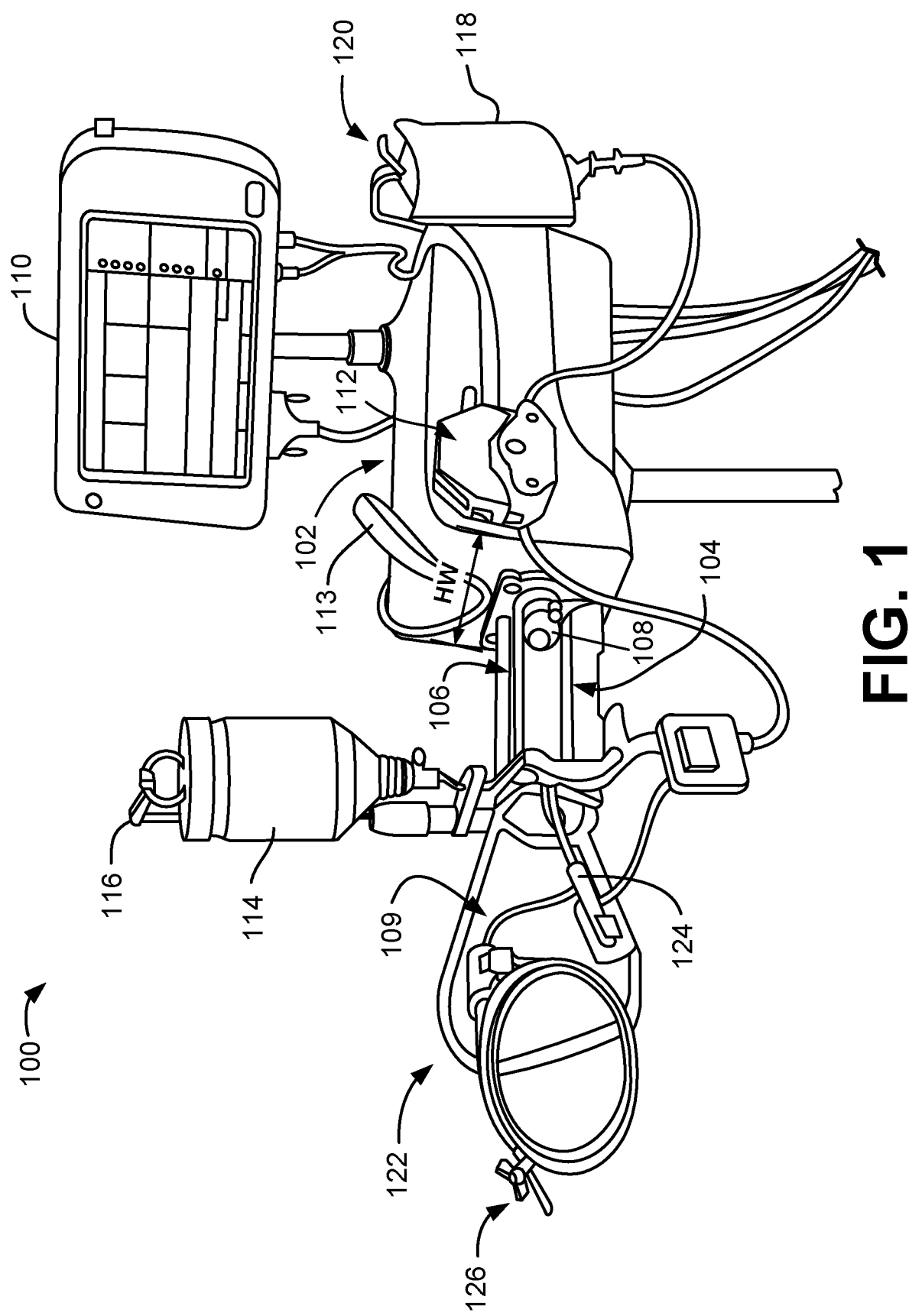
FIG. 1 is a perspective view of an exemplary embodiment of a powered fluid injector.

FIG. 1 illustrates a perspective view of an exemplary embodiment of a powered fluid injector 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures. These procedures can include, as examples, optical coherence tomography (OCT) imaging, intravascular ultrasound (IVUS) imaging, computed tomography (CT) imaging, magnetic resonance (MRI) imaging, angiographic procedures, and interventional device procedures/placements.

The illustrated powered fluid injector 100 includes a drive assembly housing 102 and a sleeve 104. The sleeve 104 can be secured to the drive assembly housing 102. For example, the drive assembly housing 102 can include an opening and the sleeve 104 can be secured to the drive assembly housing 102 at or near such opening. The sleeve 104 may extend out from the drive assembly housing 102 and may be configured to receive and hold a reservoir 106. The reservoir 106 can have an internal reservoir volume containing a fluid and include a plunger 108 within the internal reservoir volume. At least a portion of a drive assembly can be housed within the drive assembly housing 102. It is noted that the drive assembly housing 102 as shown in FIG. 1 is exemplary for purposes of generally describing features of a powered fluid injector and details related to a powered fluid injector drive assembly housing will be explained herein in reference to other figures. The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the reservoir 106, fluid within the internal reservoir volume can be pressurized and output from the reservoir 106 along tubing 109 leading to a patient. In certain applications of the powered fluid injector 100, output fluid can be pressurized anywhere from 1000-1500 psi (e.g., 1200 psi).

The illustrated embodiment of the powered fluid injector 100 includes several features that can be useful in pressurizing and delivering fluid during operation. The powered fluid injector 100 can include a control panel 110. The control panel 110 can provide a user interface for various operational aspects. For example, the control panel 110 can be utilized by an operator to set up various parameters and/or protocols to be used for a given fluid injection procedure. In one example, the operator can interact with the control panel 110 to input injection parameters such as flow rate, injection volume (e.g., maximum), injection pressure (e.g., maximum), rise time, and/or other injection parameters. In one embodiment, control panel 110 includes a touch-screen panel display, enabling an operator to view and modify injection parameters. The control panel 110 can also be used to initialize powered fluid injector 100 (e.g., to prepare it for a patient fluid injection), or to activate certain features or sequences of operation. The control panel 110 may also provide status information, including information related to past or currently ongoing injection procedures as well as any appropriate alerts. The control panel 110 can be controlled by one or more processors (e.g., at the control panel 110 itself and/or within the drive assembly housing 102). Such processors can also control other components, such as the drive assembly, a peristaltic pump 112, when present, and/or any sensors and detectors included at the powered fluid injector 100.

In addition to the control panel 110, the illustrated powered fluid injector 100 includes a hand-control device 113 for operator input. The hand-control device 113 can be coupled to the control panel 110 either wirelessly or via a lined connection. Although, in other embodiments, the hand-control device 113 can be connected to a component of powered fluid injector 100 other than control panel 110, such as drive assembly housing 102. The hand-control device 113 can generate and send various signals related to an injection procedure to the control panel 110 or other connected component. An operator can actuate one or more interface components at the hand-control device 113 to control an injection procedure. For example, the operator can use hand-control device 113 as a variable-rate control device to alter the fluid flow rate output from the powered fluid injector 100 and/or as a mechanism for starting or stopping an injection.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the reservoir 106 for use during an injection procedure. For example, fluid from the container 114 can be drawn into the reservoir 106 when the plunger 108 is being retracted (e.g., moved in a direction toward the drive assembly housing 102) and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid at a lower pressure than that at which the drive assembly delivers contrast fluid from the reservoir 106.

To facilitate delivery of fluid output from the reservoir 106 and/or peristaltic pump 112, the illustrated powered fluid injector 100 includes a module 122. The module 122 can include a valving system 124 to selectively place the reservoir 106 or peristaltic pump 112 in communication with the patient. In one example, the valving system 124 can include a manifold valve having a spring-biased spool valve, but in other examples various other types of valves, including check valves, can also be used. In one embodiment, when the valving system 124 is in a first position fluid can flow from the reservoir 106 to a patient end 126, but when valving system 124 is in a second position fluid can flow from the peristaltic pump 112 to the patient end 126. In this way, where the drive assembly outputs a relatively high pressure fluid (e.g., contrast fluid at 1000-1500 psi) from the reservoir 106 and the peristaltic pump 112 provides a relatively low pressure fluid (e.g., saline at 25-125 psi), the valving system 124 can selectively convey fluid as appropriate for a particular sequence in an injection procedure.

Figure 2:
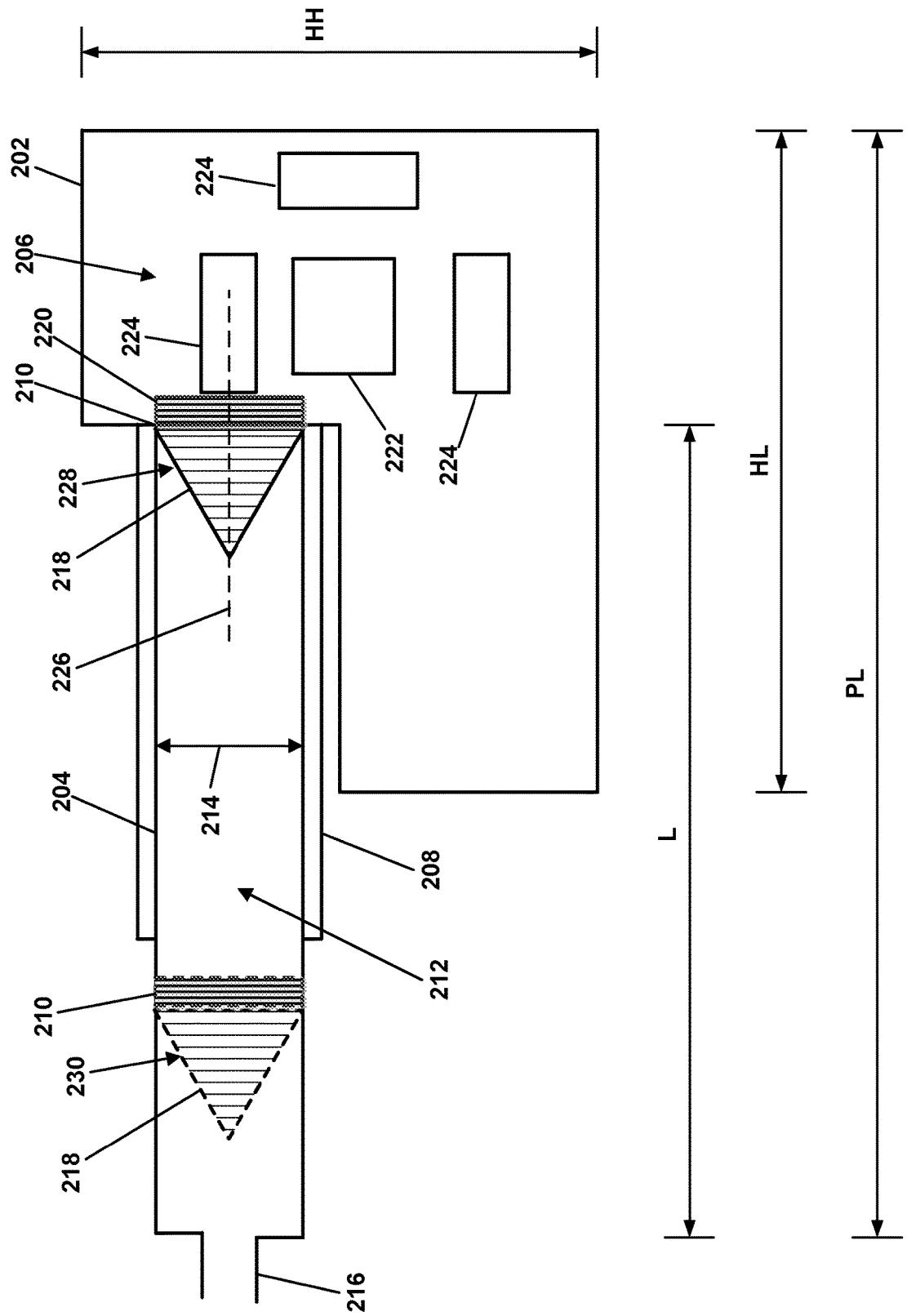
FIG. 2 is a schematic, side elevational diagram of an exemplary embodiment of a drive assembly housing for use in a powered fluid injector.

FIG. 2 illustrates a schematic, side elevational diagram of an exemplary embodiment of a drive assembly housing 202. The drive assembly housing 202 is shown here relative to a reservoir 204 and a drive assembly 206. The components shown in FIG. 2 can be used as part of a powered fluid injector, including the powered fluid injector described in reference to FIG. 1.

As shown here, a sleeve 208 can be secured to the drive assembly housing 202. In the illustrated embodiment, the drive assembly housing 202 includes an opening 210, and the sleeve 208 is secured at a region of the drive assembly housing 202 adjacent the opening 210. The sleeve 208 can be configured to receive the reservoir 204 and thereby hold the reservoir 204 relative to the drive assembly housing 202. For instance, here the sleeve 208 defines a holding region that can be sized to receive the reservoir 204 and this holding region is aligned with the opening 210 included at the drive assembly housing 202.

The reservoir 204 can include an internal reservoir volume 212. The internal reservoir volume 212 can be defined by an inner reservoir diameter 214 and a reservoir length L. The reservoir length L can extend from an end of the reservoir 204 that interfaces with the drive assembly housing 202 to an opposite end of the reservoir 204 that interfaces with an outlet 216. Thus, the reservoir length L need not include a length of the outlet 216. The internal reservoir volume 212 can contain a fluid that is to be pressurized and delivered via the outlet 216 to a patient during an injection procedure. To facilitate fluid pressurization, a plunger 218 can be movably disposed within the internal reservoir volume 212.

The drive assembly 206 can include a tip 220, an actuator 222, and a plurality of mechanical segments 224. The tip 220 has a central longitudinal axis 226 and can be configured to be secured to the plunger 218. For instance, the plunger 218 can couple to the tip 220 when the reservoir 204 is received at the sleeve 208 and interfaces with the drive assembly housing 202. A surface of the tip 220 may include one or more connection features that removably mate with one or more corresponding connection features on an interfacing surface of the plunger 218. The actuator 222 is positioned within the drive assembly housing 202 and is configured to supply a motive force for moving the tip 220. The plurality of mechanical segments 224 are configured to transmit motive force from the actuator 222 to the tip 220. In some embodiments, one of the mechanical segments 224 can be coupled to the tip 220, such as at a surface of the tip 220 that is opposite the surface secured to the plunger 218, and the other mechanical segments 224 may be coupled to one or more adjacent mechanical segments 224. Depending on the position of the tip 220, one or more (e.g., all) of the plurality of mechanical segments 224 may be positioned within the drive assembly housing 202.

The drive assembly 206 can be configured to pressurize the internal reservoir volume 212 by moving the tip 210, and thus the plunger 218, within the internal reservoir volume 212. To do so, the plurality of mechanical segments 224 can transmit motive force from the actuator 222 to the tip 220. This can act to move the tip 220 between a number of positions along the central longitudinal axis 226, including, for example, between a retracted position 228 and an extended position 230. At the retracted position 228, the tip 220 can be, for instance, at or near the drive assembly housing 202 (e.g., within the drive assembly housing 202) and the plurality of mechanical segments 224 may be within the drive assembly housing 202. At the extended position 230, the tip 220 can be positioned closer to the outlet 216 than when at the retracted position 228 and one or more of the plurality of mechanical segments 224 can be moved out from the drive assembly housing 202. As the actuator 222 moves the tip 220 from the retracted position 228 to the extended position 230, fluid within the internal reservoir volume 212 can be pressurized and delivered via outlet 216. The actuator 222 can also move the tip 220 in the opposite direction, from the extended position 230 to the retracted position 228.

The exemplary embodiment of the drive assembly housing 202 can have a number of dimensions. Namely, the drive assembly housing 202 can have a housing length HL, a housing width HW (shown in FIG. 1), and a housing height HH. The housing length HL extends in a direction parallel to the central longitudinal axis 226. The housing width HW extends in a first direction perpendicular to the central longitudinal axis 226. The housing height HH extends in a second direction perpendicular to the central longitudinal axis 226.

Together, the housing length HL and the reservoir length L can define a package length PL. The package length PL extends in a direction parallel to the central longitudinal axis 226. And, like the housing length HL, the reservoir length L extends in the direction parallel to the central longitudinal axis 226. The package length PL can be less than two times the reservoir length L (i.e., less than 2L). In some embodiments, the package length PL may be less than 1.9L, less than 1.75L, less than 1.65L, or less than 1.5L. As shown in FIG. 2, the package length PL can be measured as an extent in a direction parallel to the central longitudinal axis 226 defined by the reservoir length L and the housing length HL. The package length PL measured as such may not necessarily be equal to a total of a measured reservoir length L plus a measured housing length HL. This can be the case when the package length PL is the extent of these two components in the direction parallel to the central longitudinal axis 226 since any overlapping reservoir length L and housing length HL would account once for the extent in this direction, as is the case in the embodiment shown in FIG. 2. This package length PL results in a relatively compact powered fluid injector as compared to traditional, less compact injectors where a spatial profile of the length of the fluid container, shaft, and drive components can be more than twice the length of the fluid container itself.

To allow for a compact powered fluid injector having the described housing length HL, and thus package length PL, a variety of drive assembly embodiments can be implemented. Examples of such drive assembly embodiments are shown and described in reference to FIGS. 3-5.

Figure 3:
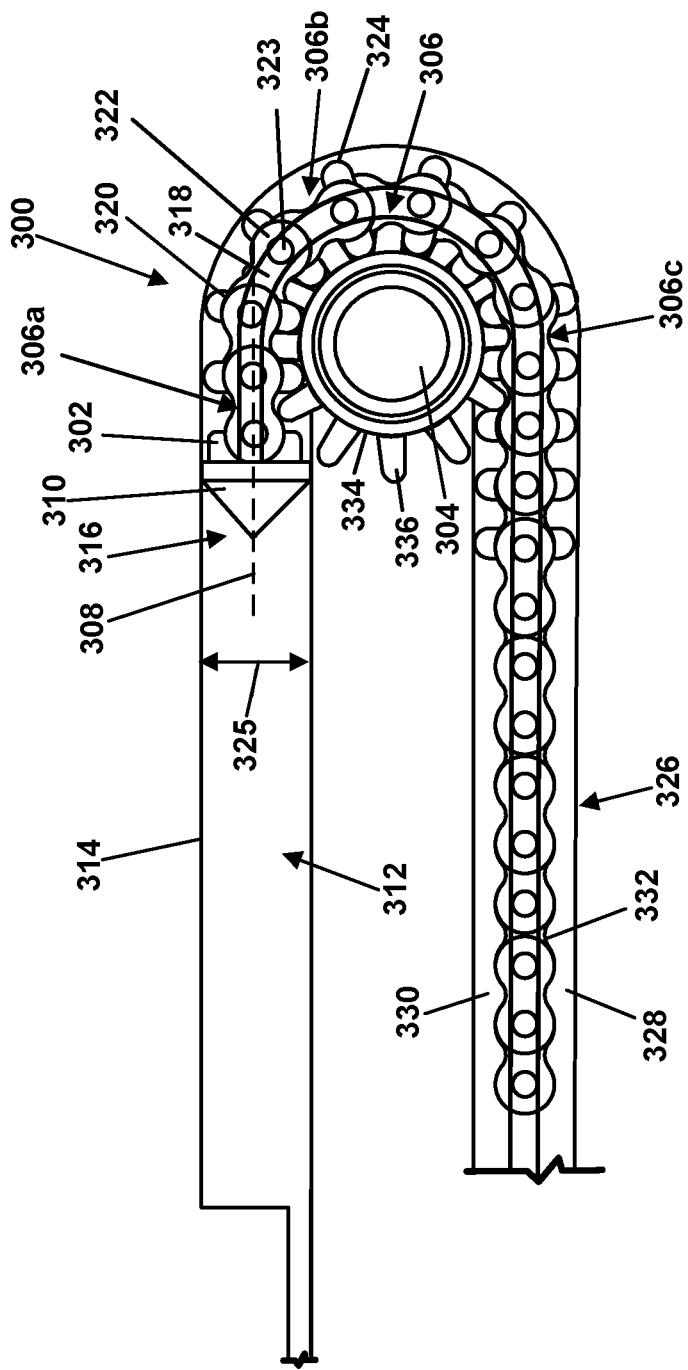
FIG. 3 is a schematic, side elevational diagram of an exemplary embodiment of a drive assembly for use in a powered fluid injector.

FIG. 3 illustrates a schematic, side elevational diagram of an exemplary embodiment of a drive assembly 300. As noted, the drive assembly 300 can be used in a powered fluid injector to allow for a housing length, and thus package length, as described in reference to FIG. 2.

The drive assembly 300 includes a tip 302, an actuator 304, and a plurality of mechanical segments 306. The tip 302 has a central longitudinal axis 308 and can be configured to be secured to a plunger 310 as described elsewhere herein. The actuator 304 is configured to supply a motive force for moving the tip 302 via the plurality of mechanical segments 306, which are configured to transmit motive force from the actuator 304 to the tip 302. In operation, the drive assembly 300 can be configured to pressurize an internal reservoir volume 312 of a reservoir 314 by moving the tip 302, and thus plunger 310, within the internal reservoir volume 312. The tip 302 is shown at a retracted position 316 and in operation can be moved between a number of positions along the central longitudinal axis 308 as described elsewhere herein.

The plurality of mechanical segments 306 includes a first segment portion 306a, a second segment portion 306b, and a third segment portion 306c. The first segment portion 306a can be along the central longitudinal axis 308 while the second segment portion 306b and the third segment portion 306c can be offset from the central longitudinal axis 308. This may be the case, for example, when the tip 302 is at the retracted position 316 as shown in FIG. 3. For instance, when the tip 302 is at the retracted position 316, the plurality of mechanical segments 306 may start at the central longitudinal axis 308 and become progressively offset from the central longitudinal axis 308 by wrapping around at least a portion of a point (e.g., within the drive assembly housing, such as the actuator 304). As shown in the example of FIG. 3, the plurality of mechanical segments 306 start at the central longitudinal axis 308 at approximately twelve o'clock on the point, here the actuator 304, and wrap around this point to approximately six o'clock where the plurality of mechanical segments 306 extend generally parallel to the central longitudinal axis 308. While the point that the plurality of mechanical segments 306 are said to wrap around at least a portion of is the actuator 304 in this example, in other examples the point could be other select components or even an arbitrary point. By wrapping the plurality of mechanical segments 306 around a point, the package length PL, can be reduced as compared to a drive assembly which utilizes a ram, or other drive member, extending linearly along the central longitudinal axis of the drive assembly tip.

Thus, when the tip 302 is at the retracted position 316 in FIG. 3, the plurality of mechanical segments 306 may define a radius of curvature that approximates a radius of the actuator 304. At this position of the tip 302, the first segment portion 306a may be tangent to a point, here the actuator 304, at a first location, the second segment portion 306b may be tangent to the same point at a second location, and the third segment portion 306c may be tangent to the same point at a third location. The first, second, and third locations can all be different from one another.

As noted, the first segment portion 306a can be along the central longitudinal axis 308 while the second segment portion 306b and the third segment portion 306c can be offset from the central longitudinal axis 308. In particular, the third segment portion 306c can be offset from the central longitudinal axis 308 at an angular degree that is greater than that at which the second segment portion 306b is offset from the central longitudinal axis 308. For instance, the second segment portion 306b can be offset from the central longitudinal axis 308 at an angle between zero and ninety degrees as measured from the central longitudinal axis 308 to a center point of the second segment portion 306b. As shown in the example here, the second segment portion 306b is offset from the central longitudinal axis 308 at an angle of about forty degrees as measured from the central longitudinal axis 308 to a center point of the second segment portion 306b. The third segment portion 306c can be offset from the central longitudinal axis 308 at an angle of ninety degrees as measured from the central longitudinal axis 308 to a center point of the third segment portion 306c. As the tip 302 is moved from the retracted position 316, the first segment portion 306a may stay along the central longitudinal axis 308 and the degree to which the second and third segment portions 306b, 306c are offset from the central longitudinal axis 308 may be reduced (e.g., the second and/or third segment portion 306b, 306c may be moved into position along the central longitudinal axis 308).

In the illustrated embodiment of the drive assembly 300, each mechanical segment of the plurality of mechanical segments 306 is in the form of a chain link member. Each chain link member can include a body 318. In some cases, each chain link member can include a pair of opposing bodies. Though an example with one body 318 is shown in FIG. 3, in an example utilizing a pair of opposing bodies, the other body of the pair of opposing bodies can be the same as the illustrated body 318. The body 318 of a chain link member can have a first end 320 and a second opposite end 322. As one example, the body 318 may have a central region between the first and second ends 320, 322 that is of a reduced width compared to that at the first and second ends 320, 322. When a pair of opposing bodies is used, the bodies can run parallel to one another and be interconnected by a pin 323. One pin 323 can connect the pair opposing bodies at the respective first end 320 of the body 318 and another pin 323 can connect the pair of opposing bodies at the respective second end 322 of the body 318.

In the drive assembly 300, each chain link member can be coupled to an adjacent chain link member to form the plurality of mechanical segments 306. For instance, the first segment portion 306a (in the form of a chain link member) is coupled to the tip 302 at its first end and to an adjacent chain link member at its second end. Each of the second segment portion 306b and third segment portion 306c (in the form of a chain link member) is coupled to an adjacent chain link member at its first end and to another adjacent chain link member at its second end. In one example, the pin 323 may serve to couple adjacent chain link members together as shown in FIG. 3. In such an example utilizing a pair of opposing bodies for each chain link member, the pin 323 can connect opposing bodies at a first end of a first chain link member, connect opposing bodies at a second end of a second chain link member, and couple the first chain link member to the second chain link member.

In some embodiments, one or more of the plurality of mechanical segments 306 can include a width that is substantially equal to an inner diameter 325 of the reservoir 314. For example, one or more of the chain link members can include an extension flange 324. The extension flange 324 may extend out from the body 318 to define a largest extent of the width of the chain link member. In the illustrated example, the extension flange 324 extends out from the body 318 at each of two opposite edges of the body 318. As one example, the extension flange 324 can extend out from the body 318 at each of the two opposite edges so that an extent of the extension flange 324, and thus width of the chain link member at this location, is substantially equal to the inner diameter 325. As shown in FIG. 3, certain of the chain link members include the extension flange 324 extending out from the body 318 at each of two opposite edges at the second end 322. In another embodiment, certain of the chain link members can include an extension flange 324 extending out from the body 318 at the first end 320, the second end 322, and/or the central region.

In the illustrated example, extension flanges 324 are included on some, but not all, of the plurality of mechanical segments 306. For example, extension flanges 324 can be included on those mechanical segment portions forming a length of the plurality of mechanical segments 306 that equals the reservoir length. In this way, when the tip 302 is moved to a fully extended position proximate an end of the reservoir 314, those mechanical segment portions that are moved into the reservoir 314 can include extension flanges 324. When present, those mechanical segment portions that will not be brought into the reservoir 314 at any possible position of the tip 302 may not include extension flanges 324.

To help support the plurality of mechanical segments 306 in the form of chain link members, the drive assembly 300 may include a chain guide 326. The chain guide 326 may be positioned within the drive assembly housing. In the illustrated example, the chain guide 326 has a first end located on the central longitudinal axis 308 (e.g., interfacing with the opening defined in the drive assembly housing and aligned with the sleeve) and a second opposite end that is offset from the central longitudinal axis 308 (e.g., by ninety degrees as measured from the central longitudinal axis 308 to a center point of the second end of the chain guide 326). The chain guide 326 can be configured to hold the plurality of mechanical segments 306 when they are within the drive assembly housing. In the illustrated example, the chain guide 326 includes a first rail 328, a second rail 330, and a slot 332 defined between the first rail 328 and the second rail 330. The body 318 of each chain link member may be positioned outside of the slot 332 and the pin 323 may sit on, and move along, the slot 332. In this way, the first and second rails 328, 330, and slot 332, are configured to slidably receive the pin 323. Similarly, if a chain link member includes the extension flange 324, the extension flange 324 may also be positioned outside of the slot 332.

The actuator 304 is configured to use the plurality of mechanical segments 306 to transmit a motive force for moving the tip 302. To do so, the actuator 304 can engage one or more of the plurality of mechanical segments 306 and thereby move the plurality of mechanical segments 306, in turn moving the tip 302. In the illustrated example, the actuator 304 includes a gear that has a surface 334 with a plurality of teeth 336 spaced along the surface 334. The gear can be rotatably driven by a power source and, when rotatably driven, the plurality of teeth 336 are configured to mesh with a number of the plurality of mechanical segments 306 to transmit motive force from the actuator 304 to the tip 302. As one example shown in FIG. 3, respective ones of the plurality of teeth 336 may engage within the central region of the body 318, or within a space defined between a pair of opposing bodies 318, of corresponding individual chain link members. For instance, in the illustrated example, the plurality of teeth 336 engage within the space defined between the pair of opposing bodies 318 of corresponding individual chain link members and use the complimentary geometry of the plurality of teeth 336 and pins 323 to move the chain link members. In FIG. 3, the plurality of teeth 336 are configured to mesh with the first segment portion 306a, in the form of a chain link member, along the central longitudinal axis 308. Also in FIG. 3, the plurality of teeth 336 are configured to mesh with the second segment portion 306b, in the form of a chain link member, at a location that is offset from the central longitudinal axis 308. In other embodiments, instead of a gear, the actuator 304 may be, for example, a fluid cylinder, stepper drive, or screw actuator.

The actuator 304 can be positioned within the drive assembly housing, for instance, at a location that is offset from the central longitudinal axis 308 therein. Positioning the actuator 304 at a location offset from the central longitudinal axis 308 can be useful for a number of reasons. For example, this location of the actuator 304 may allow for a total length of the plurality of mechanical segments 306 to be shortened as compared to a total length that would be needed if the actuator 304 were positioned along the central longitudinal axis 308. With this actuator 304 location, the plurality of mechanical segments 306 can wrap around the actuator 204 from a location that is offset from the central longitudinal axis 308 to a location that is along the central longitudinal axis 308, as shown in FIG. 3. As such, the plurality of mechanical segments 306 can be brought into alignment with the central longitudinal axis 308 by the actuator 304 without needing to have additional length present for accommodating such alignment, as can be the case if the actuator were positioned along the central longitudinal axis 308. A shortened total length of the plurality of mechanical segments 306 may allow for a shortened drive assembly housing length. As another example, this location of the actuator 304 may be useful for supporting certain of the plurality of mechanical segments 306 that are about to enter the internal reservoir volume 312. This may create additional stability and may help to prevent such mechanical segments from becoming misaligned at this time.

The drive assembly 300 can operate to move the tip 302, and thus plunger 310, between a number of positions along the central longitudinal axis 308. When operated, the actuator 304 can engage one or more of the plurality of mechanical segments 306 and thereby transfer motive force to the plurality of mechanical segments 306. This moves the plurality of mechanical segments 306 relative to reservoir 314.

For instance, when the drive assembly 300 is driven in a first operative mode, the plurality of mechanical segments 306 can be moved so as to push the tip 302 from the retracted position 316 to one or more extended positions. This can include moving the first segment portion 306a along the central longitudinal axis 308 out from the drive assembly housing and into the internal reservoir volume 312. It can also include moving one or more other segment portions (e.g., the second and/or third segment portion 306b, 306c) from one location that is offset from the central longitudinal axis 308 to another location that is along the central longitudinal axis 308. When a particular segment portion is moved into the internal reservoir volume 312, the extension flange 324, when present, can support such segment portion against the inner diameter wall of the reservoir 314.

Conversely, when the drive assembly 300 is driven in a second operative mode, the plurality of mechanical segments 306 can be moved so as to pull the tip 302 from an extended position to the retracted position 316. This can include moving the first segment portion 306a along the central longitudinal axis 308 out from the internal reservoir volume 312 and into the drive assembly housing. It can also include moving one or more other segment portions (e.g., the second and/or third segment portion 306b, 306c) from one location that is along the central longitudinal axis 308 to another location that is offset from the central longitudinal axis 308.

Figure 4:
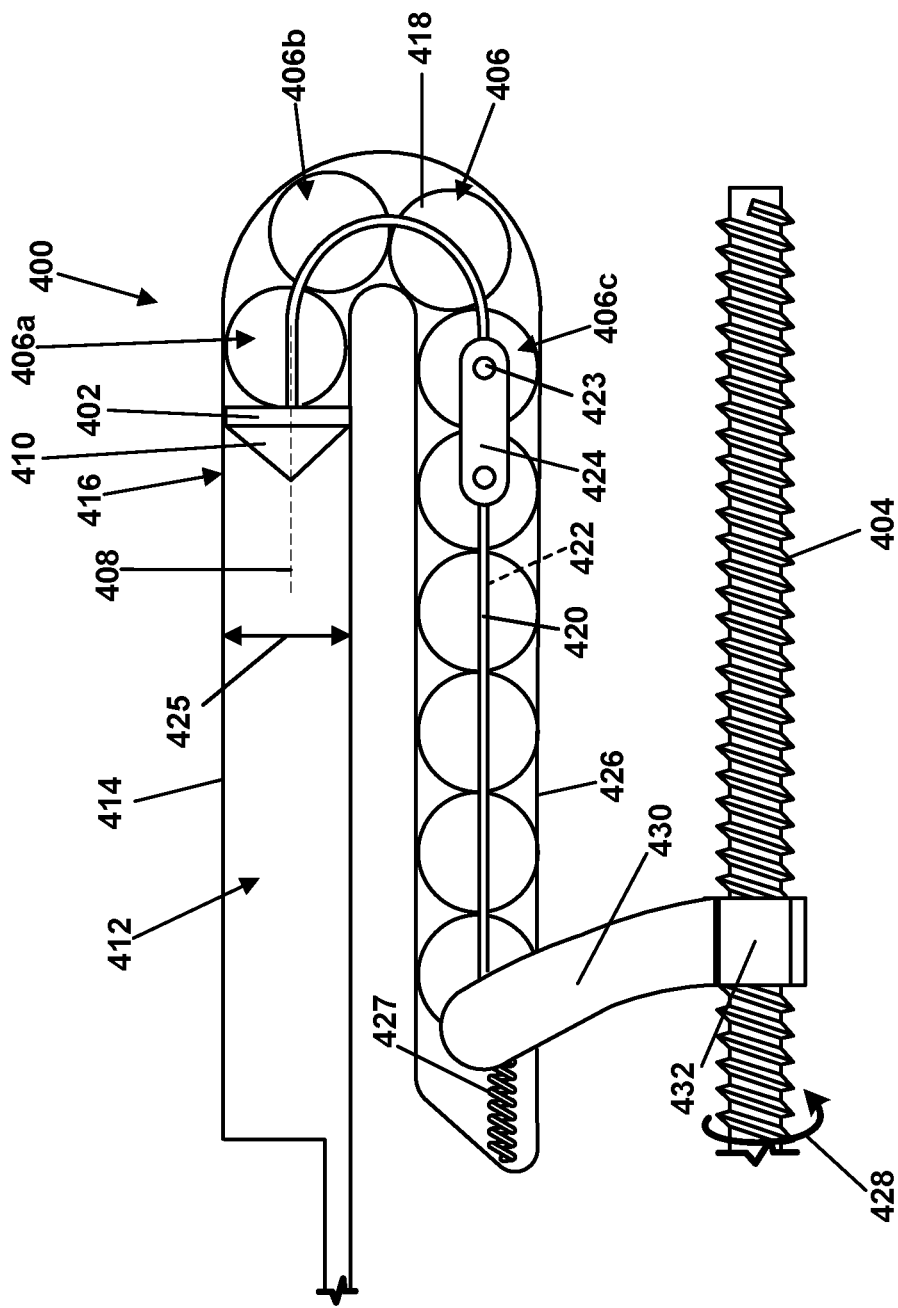
FIG. 4 is a schematic, side elevational diagram of another exemplary embodiment of a drive assembly for use in a powered fluid injector.

FIG. 4 illustrates a schematic, side elevational diagram of another exemplary embodiment of a drive assembly 400. The drive assembly 400 can be used in a powered fluid injector to allow for a housing length, and thus package length, as described in reference to FIG. 2.

The drive assembly 400 includes a tip 402, an actuator 404, and a plurality of mechanical segments 406. The tip 402 has a central longitudinal axis 408 and can be configured to be secured to a plunger 410 as described elsewhere herein. The actuator 404 is configured to supply a motive force for moving the tip 402 via the plurality of mechanical segments 406, which are configured to transmit motive force from the actuator 404 to the tip 402. In operation, the drive assembly 400 can be configured to pressurize an internal reservoir volume 412 of a reservoir 414 by moving the tip 402, and thus plunger 410, within the internal reservoir volume 412. The tip 402 is shown at a retracted position 416 and in operation can be moved between a number of positions along the central longitudinal axis 408 as described elsewhere herein.

The plurality of mechanical segments 406 includes a first segment portion 406a, a second segment portion 406b, and a third segment portion 406c. The first segment portion 406a can be along the central longitudinal axis 408 while the second segment portion 406b and the third segment portion 406c can be offset from the central longitudinal axis 408. This may be the case, for example, when the tip 402 is at the retracted position 416 as shown in FIG. 4. For instance, when the tip 402 is at the retracted position 416, the plurality of mechanical segments 406 may start at the central longitudinal axis 408 and become progressively offset from the central longitudinal axis 408 by wrapping around at least a portion of a point (e.g., within the drive assembly housing). In this example, the point that the plurality of mechanical segments 406 are said to wrap around at least a portion of is an arbitrary point within the drive assembly housing. As shown in the example of FIG. 4, the plurality of mechanical segments 406 start at the central longitudinal axis 408 at approximately twelve o'clock on the point and wrap around this point to approximately six o'clock where the plurality of mechanical segments 406 extend generally parallel to the central longitudinal axis 408. Thus, when the tip 402 is at the retracted position 416 in FIG. 4, the first segment portion 406a may be tangent to the point at a first location, the second segment portion 406b may be tangent to the same point at a second location, and the third segment portion 406c may be tangent to the same point at a third location. The first, second, and third locations can all be different from one another. By wrapping the plurality of mechanical segments 406 around a point, the package length PL, can be reduced as compared to a drive assembly which utilizes a ram, or other drive member, extending linearly along the central longitudinal axis of the drive assembly tip.

As noted, the first segment portion 406a can be along the central longitudinal axis 408 while the second segment portion 406b and the third segment portion 406c can be offset from the central longitudinal axis 408. In particular, the third segment portion 406c can be offset from the central longitudinal axis 408 at an angular degree that is greater than that at which the second segment portion 406b is offset from the central longitudinal axis 408. For instance, the second segment portion 406b can be offset from the central longitudinal axis 408 at an angle between zero and ninety degrees as measured from the central longitudinal axis 408 to a center point of the second segment portion 406b. As shown in the example here, the second segment portion 406b is offset from the central longitudinal axis 408 at an angle of about forty degrees as measured from the central longitudinal axis 408 to a center point of the second segment portion 406b. The third segment portion 406c can be offset from the central longitudinal axis 408 at an angle of ninety degrees as measured from the central longitudinal axis 408 to a center point of the third segment portion 406c. As the tip 402 is moved from the retracted position 416, the first segment portion 406a may stay along the central longitudinal axis 408 and the degree to which the second and third segment portions 406b, 406c are offset from the central longitudinal axis 408 may be reduced (e.g., the second and/or third segment portion 406b, 406c may be moved into position along the central longitudinal axis 408).

In the illustrated embodiment of the drive assembly 400, each mechanical segment of the plurality of mechanical segments 406 is in the form of a ball member. Each ball member can include a body 418. The body 418 of each ball member can be shaped to facilitate low friction movement. For instance, the body 418 can include a three-dimensional rounded outer surface, such as in the shape of a sphere.

In the drive assembly 400, each ball member can be coupled to an adjacent ball member to form the plurality of mechanical segments 406. For instance, the first segment portion 406a (in the form of a ball member) is coupled to the tip 402 at its first end and to an adjacent ball member at its second end. Each of the second segment portion 406b and third segment portion 406c (in the form of a ball member) is coupled to an adjacent ball member at its first end and to another adjacent ball member at its second end. In one embodiment, each ball member can be coupled to an adjacent ball member by a cable 420. For example, the cable 420 may be coupled to the tip 402 at a first end, extend through an aperture 422 of each ball member, and terminate at a final ball member at a second end. In another embodiment, each ball member can be coupled to an adjacent ball member by a linkage element 424. The linkage element 424 can be secured to two adjacent ball elements at an exterior surface of such ball elements using a pin 423. A linkage element can also be used to couple the first segment portion 406a to the tip 402. In a further embodiment, ball members can be coupled to adjacent ball members using both the cable 420 and one or more linkage elements.

In some embodiments, one or more of the plurality of mechanical segments 406 can include a width that is substantially equal to an inner diameter 425 of the reservoir 414. For example, one or more of the ball members can include a diameter that is substantially equal to the inner diameter 425. This can allow the ball members moved within the internal reservoir volume 412 to be supported against the inner diameter wall of the reservoir 314.

The drive assembly 400 may include a ball guide 426 supporting the plurality of mechanical segments 406 (in the form of ball members), for instance when the plurality of mechanical segments 406 are not within the internal reservoir volume 412. The ball guide 426 may be positioned within the drive assembly housing. In the illustrated example, the ball guide 426 has a first end located on the central longitudinal axis 408 (e.g., interfacing with the opening defined in the drive assembly housing and aligned with the sleeve) and a second opposite end that is offset from the central longitudinal axis 408 (e.g., by ninety degrees as measured from the central longitudinal axis 408 to a center point of the second end of the ball guide 426). The ball guide 426 can be configured to hold the plurality of mechanical segments 406 when they are within the drive assembly housing. In one example, the ball guide 426 can form an enclosed sleeve within which the ball members can move when the tip 402 is at various positions. Accordingly, to accommodate the ball members the ball guide 426 can have an interior diameter that is substantially equal to the diameter of the ball members, and thus substantially equal to the inner diameter 425 of the reservoir 414. Also, as shown in FIG. 4, the ball guide 426 includes a biasing member 427, such as a compression spring, positioned thereat. In the illustrated example, the biasing member 427 is positioned at the second end of the ball guide 426 so as to interface with a final ball member, for instance when the tip 402 is in the retracted position 416.

In the illustrated example, the actuator 404 includes a linear screw actuator configured to rotate, such as in a direction 428. An arm 430 can connect the actuator 404 to a ball member. In particular, as shown here, the arm 430 can include a fastener 432, such as a nut, at one end that connects to the actuator 404. As an example, the fastener 432 can include internal threads configured to move linearly along corresponding threads at the actuator 404 when the actuator 404 is rotated. The arm 430 can further be secured at another end to a ball member, such as the final ball member as shown in FIG. 4.

The actuator 404 and the arm 430 can be positioned within the drive assembly housing, for instance, at a location that is offset from the central longitudinal axis 408 therein. Thus, in the illustrated example, the drive assembly 400 can include a number of mechanical segments (e.g., the second segment portion 406b, the third segment portion 406c), the actuator 404, and the arm 430 positioned at a location that is offset from the central longitudinal axis 408. This can be the case such as when the tip 402 is at the retracted position 416. This can be useful, for example, by allowing for a shortened drive assembly housing length.

When the actuator 404 is rotatably driven, the arm 430 can be moved linearly along a longitudinal axis of the actuator 404 and thereby act to move the plurality of mechanical segments 406. Accordingly, the drive assembly 400 can operate to move the tip 402, and thus plunger 410, between a number of positions along the central longitudinal axis 408. When operated, the actuator 404 can transfer motive force, such as via the arm 430, to the plurality of mechanical segments 406 and thereby move the plurality of mechanical segments 406 relative to reservoir 414.

For instance, when the drive assembly 400 is driven in a first operative mode, the plurality of mechanical segments 406 can be moved so as to push the tip 402 from the retracted position 416 to one or more extended positions. This can include moving the first segment portion 406a along the central longitudinal axis 408 out from the drive assembly housing and into the internal reservoir volume 412. It can also include moving one or more other segment portions (e.g., the second and/or third segment portion 406b, 406c) from one location that is offset from the central longitudinal axis 408 to another location that is along the central longitudinal axis 408. Such first operative mode may include rotatably driving the actuator 404 in a first direction, such as the direction 428, and thereby moving the arm 430 linearly in a first direction. Conversely, when the drive assembly 400 is driven in a second operative mode, the plurality of mechanical segments 406 can be moved so as to pull the tip 402 from an extended position to the retracted position 416. This can include moving the first segment portion 406a along the central longitudinal axis 408 out from the internal reservoir volume 412 and into the drive assembly housing. It can also include moving one or more other segment portions (e.g., the second and/or third segment portion 406b, 406c) from one location that is along the central longitudinal axis 308 to another location that is offset from the central longitudinal axis 308. Such second operative mode may include rotatably driving the actuator 404 in a second direction, such as opposite the direction 428, and thereby moving the arm 430 linearly in a second direction.

Figure 5:
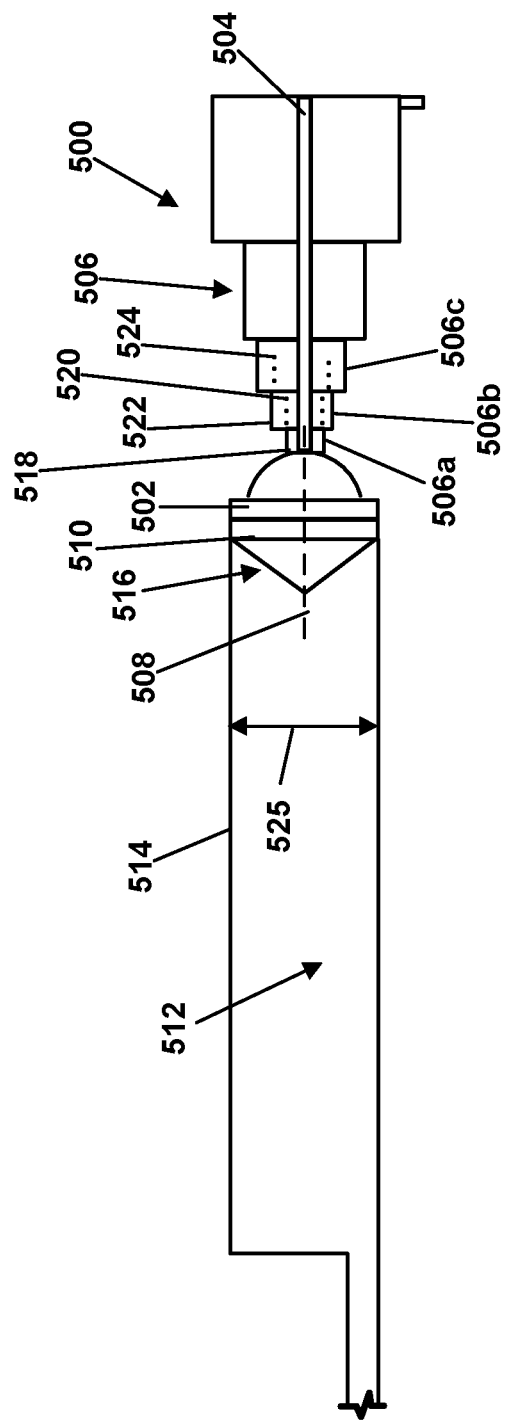
FIG. 5 is a schematic, side elevational diagram of a further exemplary embodiment of a drive assembly for use in a powered fluid injector.

FIG. 5 illustrates a schematic, side elevational diagram of a further exemplary embodiment of a drive assembly 500. The drive assembly 500 can be used in a powered fluid injector to allow for a housing length, and thus package length, as described in reference to FIG. 2.

The drive assembly 500 includes a tip 502, an actuator 504, and a plurality of mechanical segments 506. The tip 502 has a central longitudinal axis 508 and can be configured to be secured to a plunger 510 as described elsewhere herein. The actuator 504 is configured to supply a motive force for moving the tip 502 via the plurality of mechanical segments 506, which are configured to transmit motive force from the actuator 504 to the tip 502. In operation, the drive assembly 500 can be configured to pressurize an internal reservoir volume 512 of a reservoir 514 by moving the tip 502, and thus plunger 510, within the internal reservoir volume 512. The tip 502 is shown at a retracted position 516 and in operation can be moved between a number of positions along the central longitudinal axis 508 as described elsewhere herein.

The plurality of mechanical segments 506 can include a number of segment portions. For instance, the plurality of mechanical segments 506 can include a first segment portion 506a, a second segment portion 506b, and a third segment portion 506c. The first segment portion 506a can have a first diameter, measured in a direction perpendicular to the central longitudinal axis 508. The second segment portion 506b can have a second diameter, measured in the direction perpendicular to the central longitudinal axis 508. The third segment portion 506c can have a third diameter, measured in the direction perpendicular to the central longitudinal axis 508. The second diameter of the second segment portion 506b can be greater than the first diameter of the first segment portion 506a, and the third diameter of the third segment portion 506c can be greater than the second diameter of the second segment portion 506b. Where included, other segment portions of the plurality of mechanical segments 506 can be similar such that segment portion diameters can be progressively greater moving away from the tip 502.

The plurality of mechanical segments 506 can be connected and form a telescoping member. The first segment portion 506a can have a first end 518 and a second end 520 defining a first segment portion length therebetween. The second end 520 can extend within the second segment portion 506b, for instance when the tip 502 is in the retracted position 516 as shown in FIG. 5. Thus, the first diameter of the first segment portion 506a can allow at least some of the first segment portion length to nest within the second segment portion 506b having the greater diameter. The second end 520 may be movably connected within the second segment portion 506b. Likewise, the second segment portion 506b can have a first end 522 and a second end 524 defining a second segment portion length therebetween. The second end 524 can extend within the third segment portion 506c, for instance when the tip 502 is in the retracted position 516 as shown in FIG. 5. Thus, the second diameter of the second segment portion 506b can allow at least some of the second segment portion length to nest within the third segment portion 506*c* having the greater diameter. The second end 524 may be movably connected within the third segment portion 506*c*.

The actuator 504 can be configured to supply a motive force and thereby drive a telescoping sequence at the plurality of mechanical segments 506. The actuator 504 may be coupled to the first segment portion 506*a* and extend within the plurality of mechanical segments 506. In the illustrated embodiment, each of the plurality of mechanical segments 506 is along the central longitudinal axis 508. When the actuator 504 supplies a motive force, one or more of the plurality of mechanical segments 506 can be extended out from a nesting position within an adjacent segment as part of a telescoping extension sequence. The actuator may also supply a motive force to retract one or more of the plurality of mechanical segment 506 to a nesting position within an adjacent segment as part of a telescoping retraction sequence.

For example, when the tip 502 is in the retracted position 516 and the actuator 504 begins to supply motive force in a telescoping extension sequence, the first segment portion 506*a* can extend out from a nesting position within the second segment portion 506*b*. This can result in the second end 520 of the first segment portion 506*a* moving closer to the first end 522 of the second segment portion 506*b*. The extent to which the first segment portion 506*a* extends out may correspond to a degree to which the tip 502 moves along the central longitudinal axis 508 from the retracted position 516. As the actuator 504 continues to supply motive force, the second segment portion 506*b* can extend out from a nesting position within the third segment portion 506*c*. In one embodiment, the second end 520 of the first segment portion 506*a* may catch a corresponding structure of the second segment portion 506*b* and thereby urge the second segment portion 506*b* along the central longitudinal axis 508 and out from its nesting position. The extent to which the second segment portion 506*b* extends out may correspond to a degree of movement of the tip 502 along the central longitudinal axis 508 in addition to movement resulting from the first segment portion 506*a* extending out.

As the described telescoping extension or retraction sequence takes place, one or more of the plurality of mechanical segments 506 may extend within the internal reservoir volume 512. Accordingly, the first diameter of the first segment portion 506*a*, the second diameter of the second segment portion 506*b*, and/or any other segment portion diameter may each be less than an inner reservoir diameter 525 of the reservoir 514.

To supply motive force in a telescoping extension or retraction sequence but yet provide a compact injector drive assembly, a number of implementations of the actuator 504 can be used. For example, the actuator 504 can include a leadscrew that translates applied rotational force, from a motor or other power source, into linear motion. In another example, the actuator can include a shaft having a number of telescoping shaft segments that extend out from, or retract to, a nesting position within an adjacent shaft segment.

In some cases, where a powered fluid injector utilizes the drive assembly 500, the speed at which consecutive segment portions of the plurality of mechanical segments 506 are extended out may be varied. For example, during a telescoping extension sequence the actuator 504 can be configured to extend the first segment portion 506*a* out from the nesting position within the second segment portion 506*b* at a first speed. Once the first segment portion 506*a* has extended out from the nesting position within the second segment portion 506*b*, the actuator 504 can be configured to increase the speed at which the second segment portion 506*b* is extended out from the nesting position within the third segment portion 506*c*. The actuator 504 can be configured to increase the speed at which the second segment portion 506*b* is extended out to a second speed that is greater than the first speed. Likewise, as the telescoping extension sequence proceeds, the actuator 504 can be configured to progressively increase the speed at which each subsequent segment portion is extended out from its respective nesting position. A variable speed telescoping extension sequence can be useful in moving the tip 502 from the retracted position to one or more extended positions in a manner that may output a consistent fluid flow rate.

In addition to the various powered fluid injector embodiments disclosed herein, embodiments relating to methods of pressurizing a fluid are also within the scope of this disclosure. Such methods can include operating one or more of the powered fluid injector embodiments described herein.

One exemplary embodiment includes a method of pressurizing a fluid in a powered fluid injector. This method embodiment includes actuating a drive assembly of the powered fluid injector to supply a motive force for moving a tip of the drive assembly between a retracted position and an extended position. The tip can be configured to be secured to a plunger that is within an internal volume of a reservoir. At the retracted position, the tip may be closer to a drive assembly housing of the powered fluid injector than when at the extended position. At the extended position, the tip may be closer to an outlet of the reservoir than when at the retracted position. The powered fluid injector may include a drive assembly housing within which an actuator of the drive assembly is positioned. The drive assembly housing can having a housing length in a direction parallel to a central longitudinal axis of the tip and the reservoir may have a reservoir length L also in the direction parallel to the central longitudinal axis. The housing length and the reservoir length L can define a package length extending in the direction parallel to the central longitudinal axis and the package length can be less than 2L.

The method embodiment also includes moving the tip from the retracted position to the extended position. The tip is moved as such by moving a portion of the drive assembly from a first location that is offset from the central longitudinal axis of the tip to a second location that is along the central longitudinal axis of the tip. In one example, this can include moving the portion of the drive assembly between one and ninety degrees, as measured from the central longitudinal axis of the tip to a center point of the portion of the drive assembly, to bring the portion of the drive assembly from the first location to the second location. In some cases, the first location may be outside of a drive assembly housing of the powered fluid injector and the second location may be inside of the drive assembly housing of the powered fluid injector.

The method embodiment further includes moving the tip from the extended position to the retracted position by moving the portion of the drive assembly from the second location to the first location. In one example, this can include moving the portion of the drive assembly between one and ninety degrees, as measured from the central longitudinal axis of the tip to a center point of the portion of the drive assembly, to bring the portion of the drive assembly from the second location to the first location. This might also include moving the portion of the drive assembly into the drive assembly housing.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A powered fluid injector comprising:
    a sleeve configured to receive a reservoir that includes an inner reservoir diameter and a reservoir length L defining an internal reservoir volume and a plunger within the internal reservoir volume;
    a drive assembly configured to pressurize the internal reservoir volume, the drive assembly comprising:
        a tip having a central longitudinal axis and configured to be secured to the plunger, the tip having a retracted position and an extended position,
        an actuator configured to supply a motive force to the tip for moving the tip between the retracted position and the extended position, the actuator comprising a gear having a surface with a plurality of teeth spaced along the surface, and
        a plurality of mechanical segments configured to transmit the motive force from the actuator to the tip, the plurality of mechanical segments comprising a first chain link member and a second chain link member; and
    a drive assembly housing having a housing length in a direction parallel to the central longitudinal axis, a housing width in a first direction perpendicular to the central longitudinal axis, and a housing height in a second direction perpendicular to the central longitudinal axis, wherein the actuator is positioned within the drive assembly housing, and wherein the plurality of mechanical segments are positioned within the drive assembly housing when the tip is in the retracted position, and
    wherein the housing length and the reservoir length L define a package length extending in the direction parallel to the central longitudinal axis and the package length is less than 2L, and
    wherein the first chain link member is on the central longitudinal axis of the tip and the second chain link member is offset from the central longitudinal axis of the tip when the tip is in the retracted position, and wherein the plurality of teeth of the gear are configured to mesh with both the first chain link member and the second chain link member when the tip is in the retracted position, and wherein the gear is positioned such that the gear is configured to release the first chain link member as the first chain link member enters the internal reservoir volume when the tip is moved from the retracted position toward the extended position.

2. The powered fluid injector of claim 1, wherein each mechanical segment of the plurality of mechanical segments has a width equal to the inner reservoir diameter.

3. The powered fluid injector of claim 1, wherein the plurality of mechanical segments includes a first segment portion along the central longitudinal axis and a second segment portion offset from the central longitudinal axis of the tip.

4. The powered fluid injector of claim 3, wherein the plurality of mechanical segments further includes a third segment portion offset from the central longitudinal axis of the tip, the third segment portion being offset from the central longitudinal axis of the tip at an angular degree that is greater than that at which the second segment portion is offset from the central longitudinal axis of the tip.

5. The powered fluid injector of claim 4, wherein the second segment portion is offset from the central longitudinal axis of the tip at an angle between zero and ninety degrees as measured from the central longitudinal axis of the tip to a center point of the second segment portion and the third segment portion is offset from the central longitudinal axis of the tip at an angle of ninety degrees as measured rom the central longitudinal axis of the tip to a center point of the third segment portion.

6. The powered fluid injector of claim 1, wherein the plurality of mechanical segments includes a plurality of chain link members including the first chain link member and the second chain link member, each chain link member coupled to an adjacent chain link member to form the plurality of mechanical segments.

7. The powered fluid injector of claim 6, wherein the drive assembly further comprises a chain guide supporting the plurality of mechanical segments.

8. The powered fluid injector of claim 1, wherein the gear is positioned at a location that is offset from the central longitudinal axis of the tip.

9. A method of pressurizing a fluid at a powered fluid injector, the method comprising the steps of:
    actuating a drive assembly of the powered fluid injector to supply a motive force for moving a tip of the drive assembly between a retracted position and an extended position, the tip being configured to be secured to a plunger that is within an internal volume of a reservoir, the drive assembly further comprising an actuator for supplying a motive force to the tip for moving the tip between the retracted position and the extended position and a plurality of mechanical segments for transmitting the motive force from the actuator to the tip, the actuator comprising a gear having a surface with a plurality of teeth spaced along the surface, the plurality of mechanical segments comprising a first chain link member and a second chain link member;
    moving the tip from the retracted position to the extended position by engaging the first chain link member with at least one tooth of the plurality of teeth of the gear at a first location that is offset from a central longitudinal axis of the tip and engaging the second chain link member with at least one tooth of the plurality of teeth of the gear a second location that is along the central longitudinal axis of the tip, and wherein moving the tip from the retracted position to the extended position further comprises releasing the first chain link member from the at least one tooth of the plurality of teeth of the gear as the first chain link member enters the internal volume of the reservoir; and
    moving the tip from the extended position to the retracted position by moving the the second chain link member from the second location to the first location.

10. The method of claim 9, wherein the gear is positioned at a location that is offset from the central longitudinal axis of the tip.

11. The method of claim 9, wherein each mechanical segment of the plurality of mechanical segments has a width equal to an inner reservoir diameter of the reservoir.

12. A powered fluid injector comprising:
    a sleeve configured to receive a reservoir that includes an inner reservoir diameter and a reservoir length L defining an internal reservoir volume and a plunger within the internal reservoir volume;

a drive assembly configured to pressurize the internal reservoir volume, the drive assembly comprising:
  a tip having a central longitudinal axis and configured to be secured to the plunger, the tip having a retracted position and an extended position,
  an actuator configured to supply a motive force to the tip for moving the tip between the retracted position and the extended position, the actuator comprising a gear having a surface with a plurality of teeth spaced along the surface, and
  a plurality of mechanical segments configured to transmit the motive force from the actuator to the tip, the plurality of mechanical segments comprising a first chain link member and a second chain link member, wherein at least one of the first chain link member and the second chain link member includes a body and an extension flange that extends out from the body to define a largest extent of a width of the at least one of the first chain link member and the second chain link member, and wherein the extension flange is configured to support the at least one of the first chain link member and the second chain link member against the internal reservoir diameter when the tip is in the extended position; and
a drive assembly housing having a housing length in a direction parallel to the central longitudinal axis, a housing width in a first direction perpendicular to the central longitudinal axis, and a housing height in a second direction perpendicular to the central longitudinal axis, wherein the actuator is positioned within the drive assembly housing, and wherein the plurality of mechanical segments are positioned within the drive assembly housing when the tip is in the retracted position, and
wherein the housing length and the reservoir length L define a package length extending in the direction parallel to the central longitudinal axis and the package length is less than 2L, and
wherein the first chain link member is on the central longitudinal axis of the tip and the second chain link member is offset from the central longitudinal axis of the tip when the tip is in the retracted position, and wherein the plurality of teeth of the gear are configured to mesh with both the first chain link member and the second chain link member when the tip is in the retracted position.

13. The powered fluid injector of claim 12, wherein the gear is positioned such that the gear is configured to release the first chain link member as the first chain link member enters the internal reservoir volume when the tip is moved from the retracted position toward the extended position.

14. The powered fluid injector of claim 12, wherein the drive assembly further comprises a chain guide supporting the plurality of mechanical segments.

15. The powered fluid injector of claim 12, wherein the gear is positioned at a location that is offset from the central longitudinal axis of the tip.

* * * * *